(12) United States Patent
Cui

(10) Patent No.: US 6,867,318 B1
(45) Date of Patent: Mar. 15, 2005

(54) COMPOSITION FOR COATING OF ALUMINUM

(75) Inventor: Ji Cui, Evanston, IL (US)

(73) Assignee: Nalco Company, Naperville, IL (US)

( * ) Notice: Subject to any disclaimer, the term of this patent is extended or adjusted under 35 U.S.C. 154(b) by 0 days.

(21) Appl. No.: 10/881,902

(22) Filed: Jun. 30, 2004

(51) Int. Cl.$^7$ .................................................. C07F 7/10
(52) U.S. Cl. .................... 556/423; 106/287.11; 528/28; 427/387; 427/388.1; 427/372.2
(58) Field of Search ...................... 556/423; 106/287.11; 523/25; 427/387, 388.1, 372.2

(56) References Cited

U.S. PATENT DOCUMENTS

| 5,270,428 | A | 12/1993 | Castellucci |
| 6,261,638 | B1 | 7/2001 | van Ooij et al. |
| 6,733,579 | B1 | 5/2004 | Górecki |

FOREIGN PATENT DOCUMENTS

| EP | 0 570 173 A2 | 11/1993 |
| WO | WO 01/12876 A1 | 2/2001 |
| WO | WO 03/002057 A2 | 1/2003 |

Primary Examiner—Samuel Barts
(74) Attorney, Agent, or Firm—Michael B. Martin; Thomas M. Breininger

(57) ABSTRACT

A composition of matter of formula TG13-R

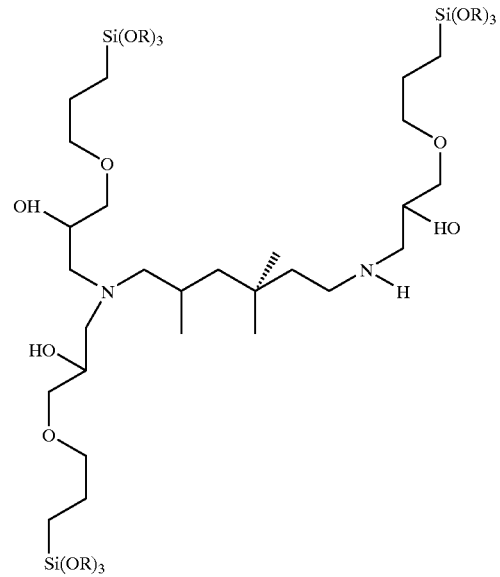

and a composition of matter of formula TG14-R

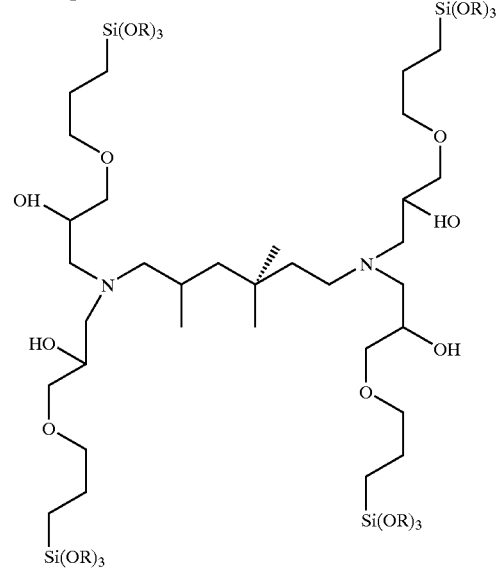

where R is H or $C_1$–$C_6$ alkyl, is described and claimed. These compositions of matter have been found to be useful in a Coating Mixture that is applied to aluminum or aluminum alloys.

9 Claims, No Drawings

COMPOSITION FOR COATING OF ALUMINUM

FIELD OF THE INVENTION

This invention is in the field of coatings for metals. The coating is useful on aluminum and aluminum alloys.

BACKGROUND OF THE INVENTION

Aluminum and aluminum alloy metals typically need to be coated otherwise they rust or display other undesirable effects from exposure to atmosphere and moisture.

Chromating has been the method of choice in aluminum finishing and aerospace industry for pretreating of all types of aluminum alloys for many decades. The chromate conversion coating formed on aluminum surface serves two basic purposes: stand-alone temporary protection of the metal against corrosion and as a base for adhesion to paint overcoat. The former is achieved via electrochemical and barrier passivation of aluminum by an $Al_2O_3$—$Cr_2O_3$ mixed oxide layer, and the latter owes, in large part, to increased surface area of chromated surface. The chromating reaction proceeds by Cr(VI) oxidizing the Al to Al (III), which forms an amorphous mixed oxide layer. This reaction is by no means stoichiometric, and excess Cr(VI) are often present in the resultant oxide film. When fresh metal surface is exposed as a result of physical impact and at suitable humidity levels, the remnant Cr(VI) in the film can slowly leach out to oxidize and seal the "wound", a phenomenon known as "self-healing". Nonetheless, use of chromates is under ever-tightening regulations because chromate has been identified as a human carcinogen.

Exploring health/environment-benign alternatives to chromates with comparable corrosion protection performance has been underway for well over a decade. To date, the new types of chemistry investigated have only partially met the goal. Those proposed new conversion coatings often necessitate using other transition metals (although less toxic), and/or fail to meet the same performance standard set by chromates in terms of both stand-alone protection and paint adhesion.

Among different conversion coating systems examined, silane-based one possesses several valuable characteristics. Silane based coatings are completely metal-free (therefore truly "green"), and they can covalently bind the paint to the metal, leading to superior paint adhesion. Organofunctional silanes have long been used as coupling agents for binding two surfaces of different chemistries, such as fiberglass to plastics and rubber to metals. Commonly referred to as "organic-inorganic hybrid" compounds, organofunctional silanes have reactive organic functional groups on one end (such as epoxy, amino, acryl, etc.) and hydrolysable alkoxysilyl groups on the other. Coupling to paint resins is effected via reaction between the organic functional groups of the silane and those of resin molecules; while coupling to metal surfaces occurs via formation of metal-oxygen-silicon, or M—O—Si bonds, where M is equal to metal. When applied from water solution at acidic pH, the hydrophobic alkoxysilyl group of the silane hydrolyzes to hydrophilic silanol groups that are more compatible, in terms of surface energy, with that of hydrophilic metal oxide surfaces.

Investigation on using silane coupling agents as replacement to chromates has been pioneered by Van Ooij et al. Initial efforts of other research groups were largely confined to monofunctional silane, i.e., silane with one hydrolysable alkoxysilyl group. Monofunctional silane —X—R—Si—$(OR')_3$, where X is the organic functional group, tends to form a linear siloxane polymer with pendant silanol groups upon controlled hydrolysis. This might suggest that further condensation via those pendant silanols should give rise to a well crosslinked barrier film. However, it was found that the property of monofunctional silane-derived coating is hardly satisfactory without using additional crosslinkers such as tetraethoxysilane (TEOS) or tetravalent Zr, and the applicable life of the coating solution is very short. Problematic still, in diluted water solutions, the monofunctional silanes also tend to form a monolayer on hydroxylated or silaceous surfaces via M—Si—O bonds, leaving no —Si$(OR')_3$ groups available to crosslink with other silane molecules and unable to build up a thicker film that is essential to corrosion protection.

The Van Ooij group has determined that multifunctional silanes (silanes with more than one alkoxysilyl groups) are much effective at forming protection layer on aluminum. This finding underscores the importance of film-forming properties of the silanes when it comes to corrosion protection of unpainted metals. It is believed, without intending to be bound thereby, that corrosion of a coated metal surface involves diffusion of corrosive species from environment to the paint/metal interface, which can be hindered when the diffusion path is made tortuous and diffusivity reduced by high degree of crosslinking of the coating layer.

The situation is very different in the case of bifunctional silanes, denoted as $(R'O)_3$—Si—R—Si—$(OR')_3$, where R is a bridging group with or without heteroatoms. This bifunctional silane is capable of covalently binding to the native metal oxide on metal surfaces through one of the two alkoxysilyl groups and of condensing/crosslinking among themselves through the other. The nature of thus crosslinked matrix is no longer that of a siloxane, but of an organic/inorganic hybrid material.

Bis-type silanes reported in literature for use in corrosion protection of metals include bis-(3-triethoxysilylpropyl)tetrasulfane(BTSPS), bis-1,2-[triethoxysilyl]ethane (BTSE), bis-1,2-[trimethoxylsilylpropyl]amine (BTSPA), all of which are commercially available. BTSE was the first bis-functional silane explored and was soon discarded due to lack of reactive organic functional groups on the backbone ethylene group that is essential for paint adhesion. The sulfidesilane-BTSPS had been investigated as a protection layer on various grades of steel and aluminum alloys. A series of corrosion tests including neutral and copper accelerated salt spray, paint adhesion, hot salt immersion, as well as several electrochemical characterization demonstrated that overall performance of BTSPS is equivalent to, sometimes better than that of chromate conversion coating. It is believed that interaction between the sulfide —$(S_4)$— and Fe atom significantly contributes to the electrochemical passivation of steel, and interaction between $S_4$ group and topcoat functional residues enhances the adhesion of the silane layer to paints and rubbers. Although BTSPS also protects aluminum and zincated surfaces as well as it does to steel, it suffers two major drawbacks. It is solvent-borne and requires lengthy (often days of) hydrolysis prior to application due to its high hydrophobicity. Furthermore, although the bisamino silane-BTSPA is totally water soluble without any organic solvent, its corrosion protection performance of unpainted aluminum is far inferior to that of tetrasulfide silane. This can be partially explained by its lower hydrophobicity due to the presence of hydrophilic secondary amine group. Adding vinyltriacetoxylsilane-VTAS to BTSPA solution helps raise its performance to a certain degree, but the vinyl silane is not stable in water and is observed to slowly condense and precipitate out of solution over time.

The key to a successful silane-based metal pretreatment process lies in identifying a multifunctional silane with an ideal combination of water solubility (a practical issue), hydrophobicity (for best corrosion protection), high crosslinking capabilities (barrier to diffusion of corrosive species), slow rate of condensation (long solution life), and reactivity (for paint adhesion). However, neither tetrasulfide nor bisamino silane can meet all five requirements, nor can any current commercial silanes. Therefore, it would be desirable to identify new metal coatings that are useful to coat aluminum and aluminum alloys.

SUMMARY OF THE INVENTION instant claimed invention is a composition of matter of formula TG 13-R:

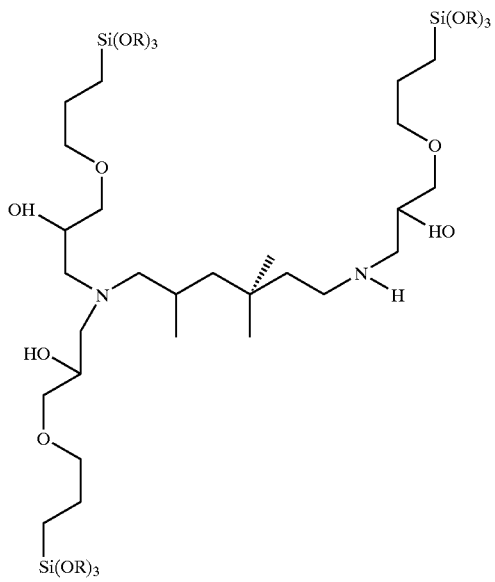

where R is H or $C_1$–$C_6$ alkyl.

The second aspect of the instant claimed invention is a composition of matter of formula TG 14-R:

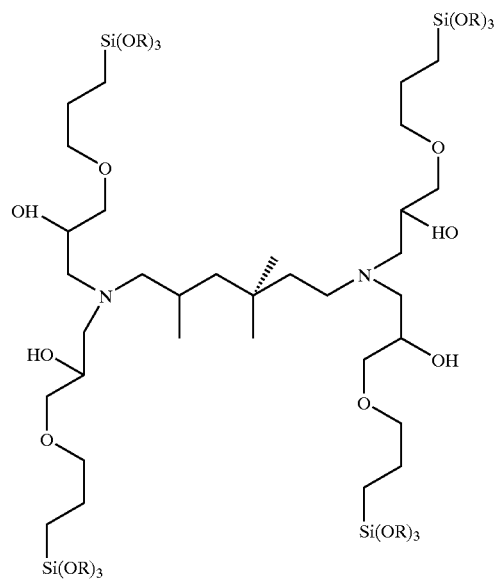

where R is H or $C_1$–$C_6$ alkyl.

The third aspect of the instant claimed invention is a method of coating metal comprising a) cleaning the surface of the metal with a cleaner;
b) coating the surface of the metal with a Coating Mixture; and
c) thermally annealing the Coating Mixture on the surface of the metal to form a crosslinked coating;

wherein the Coating Mixture comprises a composition of matter of formula TG13-R:

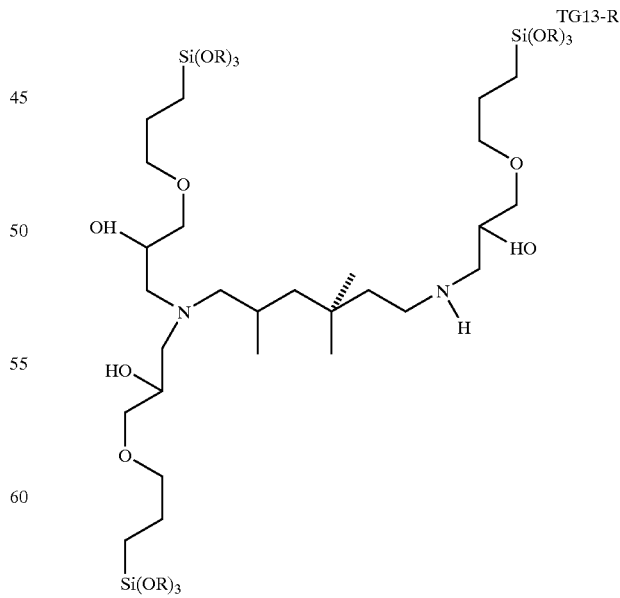

where R is H or $C_1$–$C_6$ alkyl;

or a composition of matter of formula TG14-R:

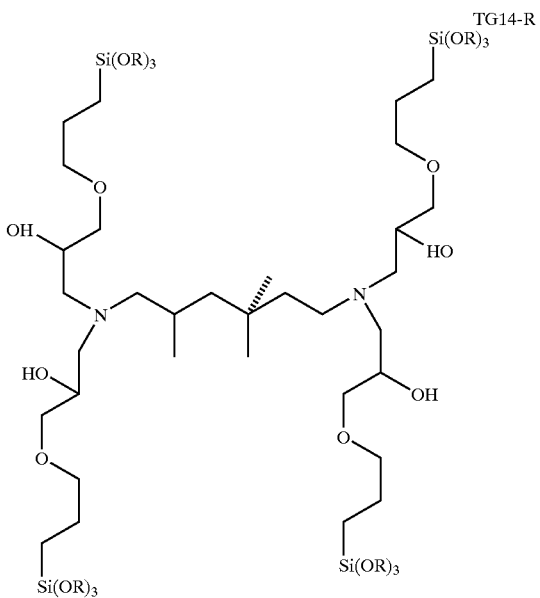

where R is H or $C_1$–$C_6$ alkyl; or a combination thereof; and where the metal is aluminum or an aluminum alloy.

DETAILED DESCRIPTION OF THE INVENTION

Throughout this patent application, the following terms have the indicated meanings.

"Alkyl" means a monovalent group derived from a straight chain saturated hydrocarbon by the removal of a single hydrogen atom. $C_1$–$C_6$ Alkyl means alkyl selected from the group consisting of methyl, ethyl, n-propyl, n-butyl, n-pentyl and n-hexyl.

"Nalco" means Nalco Company, 1601 W. Diehl Road, Naperville, Ill. 60563. (630) 305-1000.

The first aspect of the instant claimed invention is a composition of matter of formula TG13-R:

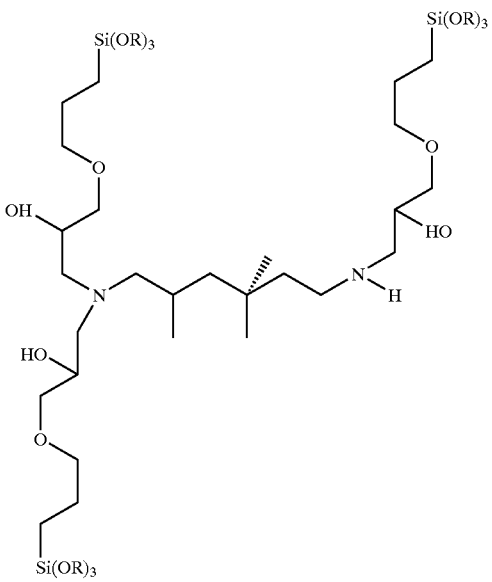

Where R is H or $C_1$–$C_6$ alkyl,

TG13-R is formed by reacting an epoxy silane and an aliphatic diamine in a molar ratio of 3:1 epoxy silane to aliphatic diamine.

When R is methyl, the epoxy silane is 3-glycidoxypropyltrimethoxysilane and the aliphatic diamine is C,C,C,-trimethyl-1,6-hexanediamine.

When R is ethyl, the epoxy silane is 3-glycidoxypropyltriethoxysilane and the aliphatic diamine is C,C,C,-trimethyl-1,6-hexanediamine.

When R is n-propyl, the epoxy silane is 3-glycidoxypropyltripropoxysilane and the aliphatic diamine is C,C,C,-trimethyl-1,6-hexanediamine.

When R is n-butyl, the epoxy silane is 3-glycidoxypropyltributoxysilane and the aliphatic diamine is C,C,C,-trimethyl-1,6-hexanediamine.

When R is n-pentyl, the epoxy silane is 3-glycidoxypropyltripentoxysilane and the aliphatic diamine is C,C,C,-trimethyl-1,6-hexanediamine.

When R is n-hexyl, the epoxy silane is 3-glycidoxypropyltrihexoxysilane and the aliphatic diamine is C,C,C,-trimethyl-1,6-hexanediamine.

C,C,C,-trimethyl-1,6-hexanediamine, 3-glycidoxypropyltrimethoxysilane and 3-glycidoxypropyltriethoxysilane are all available commercially. 3-glycidoxypropyltripropoxysilane, 3-glycidoxypropyltributoxysilane, 3-glycidoxypropyltripentoxysilane, and 3-glycidoxypropyltrihexoxysilane can be synthesized using techniques known to people of ordinary skill in the art.

The reaction optimally takes place in an equal amount of a suitable solvent, such as a suitable alcohol. Suitable alcohols include, but are not limited to, methyl alcohol and ethyl alcohol. A preferred alcohol is methyl alcohol.

The mixture is allowed to react at room temperature, about 21° C., for from about 24 to about 48 hours. If time is an issue, the mixture is allowed to react at about 70° C. for about 3 hours. For either synthetic route, the yield is high, usually above 95% (on amine basis).

TG13-R and TG14-R can also be synthesized when R is hydrogen, abbreviated "H". This synthesis involves first making TG13-R or TG14-R where R is $C_1$–$C_6$ alkyl and then hydrolyzing TG13-R and TG14-R in water for from about 2 to about 24 hours. The composition of matter where R is H is a silanol, and silanols are known to be relatively unstable. Therefore, if it is desired to make the composition of matter where R is hydrogen, then it must be understood that this composition must be applied to metal as soon as the synthesis has been completed.

The preferred composition of matter of formula TG13-R is when R is methyl. This composition is depicted in formula TG13.

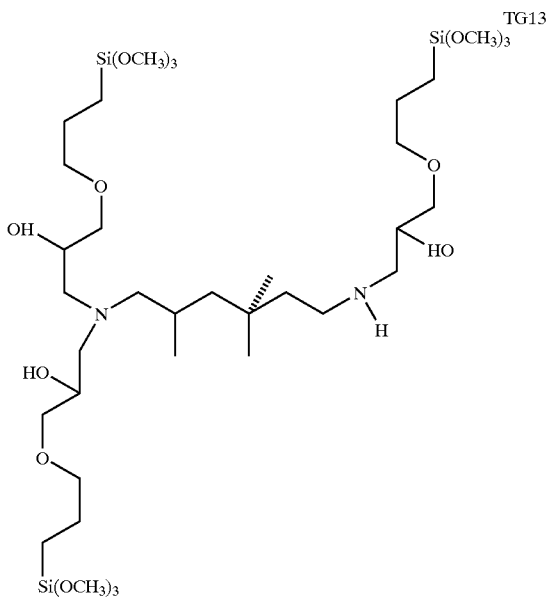

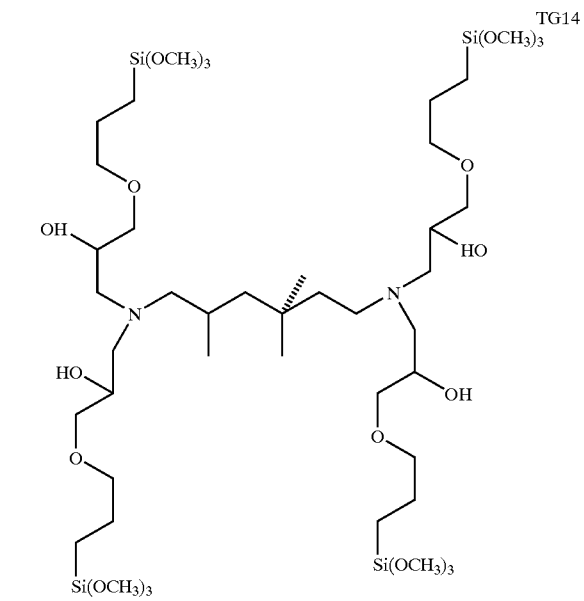

The second aspect of the instant claimed invention is a composition of matter of formula TG14-R:

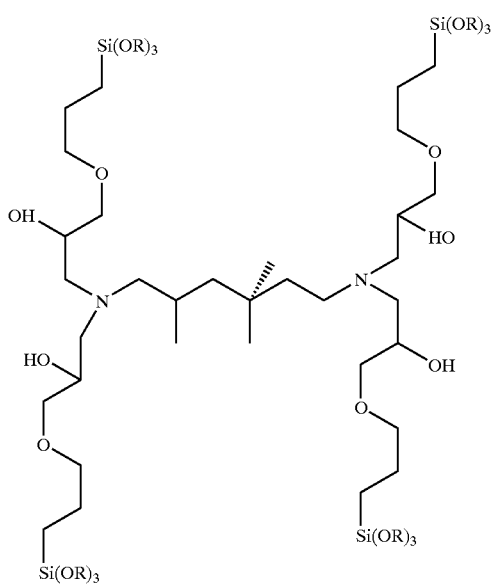

where R is H or $C_1$–$C_6$ alkyl.

The composition of matter of formula TG14-R is formed by reacting an epoxy silane and an aliphatic diamine in a molar ratio of 4:1 epoxy silane to aliphatic diamine. The epoxy silane and aliphatic diamine are the same as for the synthesis of TG13-R. The synthetic method is also the same as that for the synthesis of TG14-R, with the change being in the molar ratio of epoxy silane to aliphatic diamine.

The preferred composition of matter of formula TG 14-R is when R is methyl. This composition is depicted in formula TG14.

A Coating Mixture comprising a composition of matter of formula TG13-R or a composition of matter of formula TG14-R or a combination thereof has been found to be useful in coating aluminum or aluminum alloys.

The third aspect of the instant claimed invention is a method of coating a metal comprising a) optionally cleaning the surface of the metal with a cleaner;

b) coating the surface of the metal with a Coating Mixture;

c) thermally annealing the Coating Mixture on the surface of the metal to form a crosslinked coating;

wherein the Coating Mixture comprises a composition of matter of formula TG13-R:

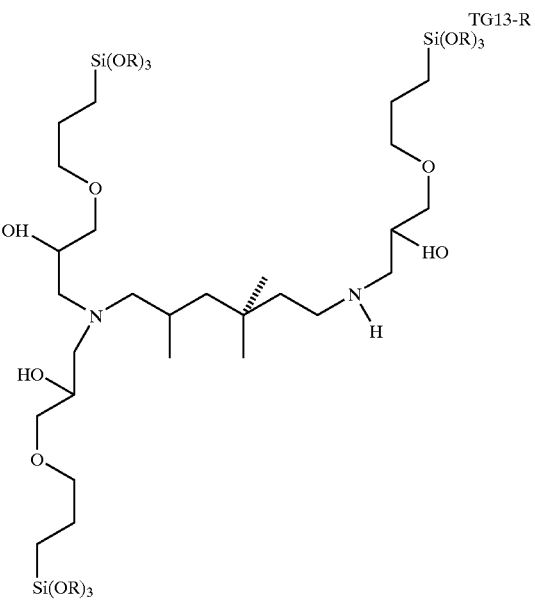

where R is H or $C_1$–$C_6$ alkyl;

or a composition of matter of formula TG14-R:

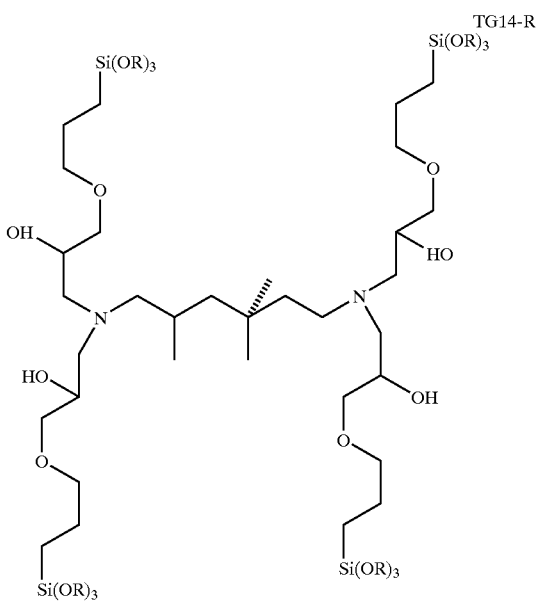

where R is H or $C_1$–$C_6$ alkyl;
or a combination thereof; and
wherein the metal is aluminum or an aluminum alloy.

The metals are selected from the group comprising aluminum and aluminum alloys. Commercially available aluminum and aluminum alloys include, but are not limited to, the following: sheet forming alloys 2024, 7075, 6061, 6111, 1100, 3003, 3015, 5086, 5052 and cast forming alloy 356. These aluminum and aluminum alloys are available from ACT Laboratory.

The surface of the metal may optionally be cleaned using techniques known in the art of aluminum cleaning. In practice, it is preferred that the metal be cleaned before it is coated with the Coating Mixture.

In order to make a composition of matter of either formula TG13-R or formula TG14-R or a combination thereof water soluble, the formula must be neutralized with a stoichiometric amount of suitable acid. One such suitable acid is acetic acid.

Once the composition of matter has been rendered water soluble, any coating made therefrom should have low volatile organic compound ("VOC") emissions.

In addition to containing the composition of matter TG13R or TG14R or a combination thereof, the Coating Mixture may contain other ingredients commonly found in coatings used on aluminum or aluminum alloys. These ingredients may include biocides, corrosion inhibitors, pigments, rheology modifiers and surfactants. These formulated coatings may also include other functional ingredients known in the metal coatings industry.

The Coating Mixture may be applied as a coating by any known coating method, including dipping, spraying, brush application or any other coating technique.

In a typical coating process, the metal is
(a) cleaned,
(b) rinsed
(c) coated, and then
(d) thermally cured.

It is recommended that a coating thickness of at least from about 0.1 microns to about 1.0 microns be applied to the surface of the aluminum or aluminum alloy. A very useful feature of this Coating Mixture is that the Coating Mixture is compatible with existing coating equipment.

The Coating Mixture on the surface of the metal is thermally annealed by exposing the coated aluminum to heat for from about 10 minutes to about 16 hours, to form a crosslinked coating. The amount of time for annealing within that range depends upon the annealing temperature. Typical annealing temperatures range from room temperature of about 20° C. to an elevated temperature of about 120° C. The relationship between time and annealing temperature is this: the hotter the annealing temperature, the less time it takes to anneal the coating and the cooler the annealing temperature, the more time it takes to anneal the coating.

Another useful feature of this Coating Mixture is that the Coating Mixture, as described herein, does not require any chromium metal to make it an effective Coating Mixture.

Another useful feature of this Coating Mixture is that an aqueous 5% wt. solids Coating Mixture, where R is $C_1$–$C_6$ alkyl, and not H, has been found to exhibit stable shelf life of at least about 3 weeks without exhibiting any degradation of anticorrosion performance for painted metal.

Another useful feature of the instant claimed invention is that an aqueous 5% wt. solids Coating Mixture containing the TG14 composition of matter has been found to yield a thin, clear coating, which is invisible to the eyes, and therefore does not interfere with the metal's natural luster. Interference with the natural luster of the metal has been found when a chromium containing coating is used.

It has been found that the Coating Mixture formed with a 4:1 epoxy silane-aliphatic diamine molar ratio performed well in salt spray corrosion tests. Coatings formed with the instant claimed Coating Mixtures exhibit an overall performance comparable or superior to chrome-based conversion coatings for certain types of aluminum alloys, either bare or painted.

The foregoing may be better understood by reference to the following Examples, which are presented for purposes of illustration and are not intended to limit the scope of this invention.

EXAMPLES

Example 1a

Synthesis of TG13

A 3:1 molar ratio of 3-glycidoxypropyltrimethoxysilane (GPS) and C,C,C-trimethyl-1,6-hexanediamine(TMH) is added to an equal weight of ethyl alcohol. The mixture is allowed to react at 70° C. for 3 hours. The reaction products are subsequently neutralized with a 20% excess (based on stoichiometry) of acetic acid.

Example 1b

Testing of TG13

The neutralized silane concentrate of Example 1a is diluted with water to 5% silane (by weight) and applied to aluminum panels by dip-coating.

The panels dip coated with this Coating Mixture are first baked in an oven at 120° C. for about 0.5 hours and then further coated with about 20 microns of white polyester based paint, obtained from Sherwin Williams Coatings Company. The white painted panels are then subjected to an ASTM BI 17 condition Neutral Salt Spray Corrosion test. After 3000 hours of salt spray, no paint loss or blistering is found along the scribe lines.

The conclusion reaches is that the Coating Mixture comprising TG13 bonds the paint to aluminum very well even when the aluminum is exposed to humid and corrosive conditions.

Example 2

Example 2a

Synthesis of TG14

A 4:1 molar ratio of 3-glycidoxypropyltrimethoxysilane (GPS) and C,C,C-trimethyl-1,6-hexanediamine(TMH) is added to an equal weight of ethyl alcohol. The mixture is allowed to react at 70° C. for 3 hours. The reaction products are subsequently neutralized with a 20% excess (based on stoichiometry) of acetic acid.

Example 2b

First Testing of TG14

The neutralized silane concentrate of Example 2a is diluted with water to 5% silane (by weight) and applied to aluminum panels by dip-coating.

The coated aluminum panels are found to tolerate over 360 hours of salt spray (tested according to ASTM B117) without showing any signs of corrosion, equivalent in performance to conventional chrome-based conversion coating.

In contrast to the results obtained using the Coating Mixture of the instant claimed invention, bare Al panels start to corrode in 6 hours. Other commercially available silane based coatings failed at 96 hours (bis-[trimethoxysilyl] amine and vinyltriacetoxysilane mixture) and 240 hours (structures of 3-glycidoxypropyltrimethoxysilane and N-(2-aminoethyl)$_3$-aminopropyltrimethoxysilane).

Example 2c

Second Testing of TG14

In a second test, the neutralized silane concentrate of Example 2a is diluted with water to 5% silane (by weight) and applied to aluminum panels by dip-coating. The panels dip coated with this TG14 Coating Mixture are first baked in an oven at 120° C. for about 0.5 hours and then further coated with about 20 microns of white polyester based paint, obtained from Sherwin Williams Coatings Company. The white painted panels are then subjected to an ASTM B 117 condition Neutral Salt Spray Corrosion test. After 3000 hours of salt spray, no paint loss or blistering is found along the scribe lines.

Various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A composition of matter of formula TG 13-R:

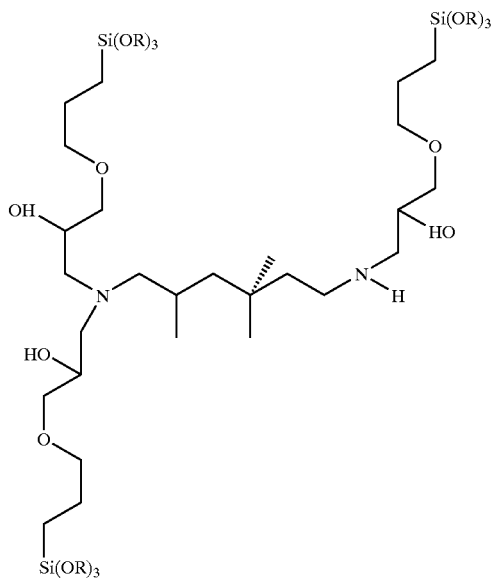

where R is H or $C_1$–$C_6$ alkyl.

2. A composition of matter of formula TG 14-R:

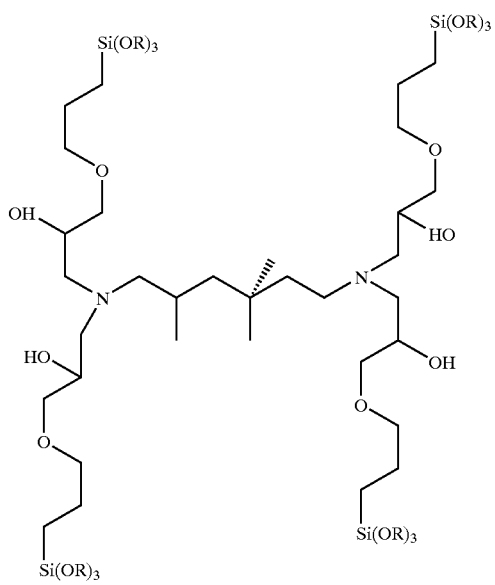

where R is H or $C_1$–$C_6$ alkyl.

3. A composition of matter of formula TG13:

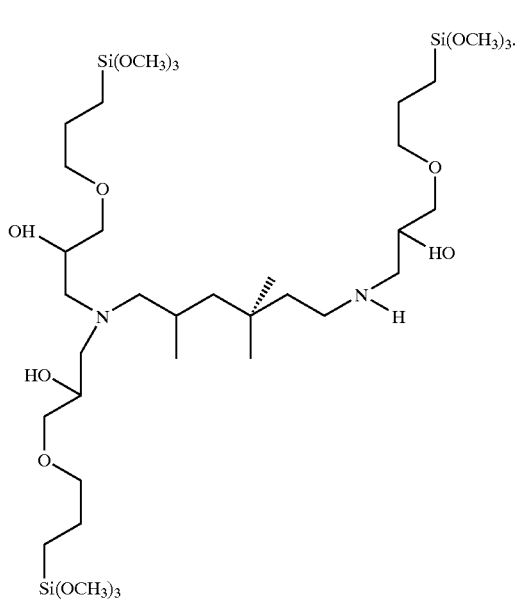

4. A composition of matter of formula TG14:

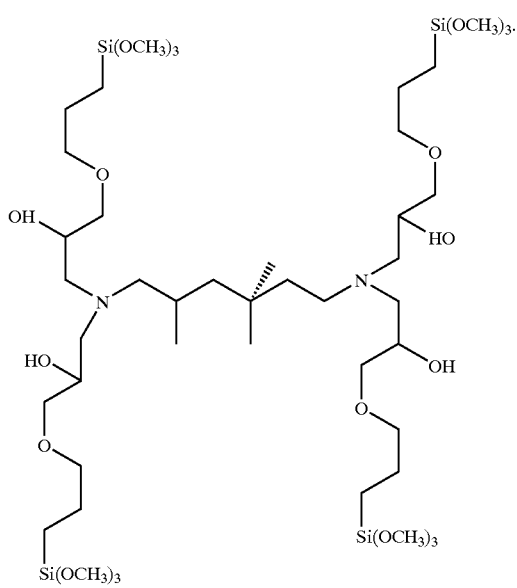

5. A method of coating a metal comprising
(a) optionally cleaning the surface of the metal with a cleaner;
(b) coating the surface of the metal with a Coating Mixture; and
(c) thermally annealing the Coating Mixture on the surface of the metal to form a crosslinked coating;
wherein the Coating Mixture comprises a composition of matter of formula TG13-R:

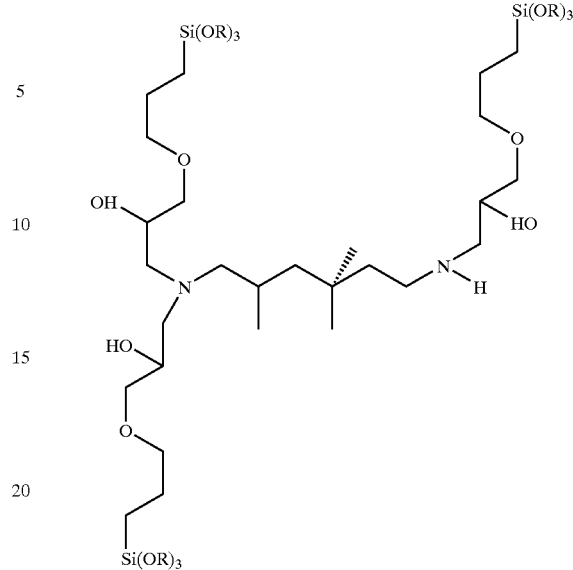

where R is H or $C_1$–$C_6$ alkyl;
or a composition of matter of formula TG 14-R:

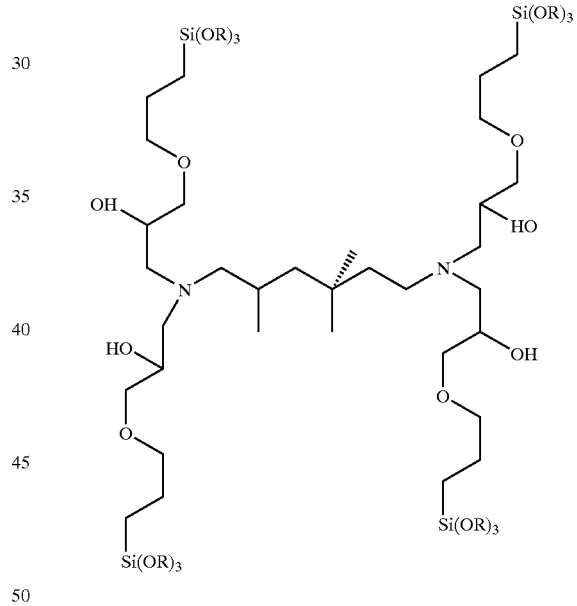

where R is H or $C_1$–$C_6$ alkyl; or a combination thereof; and wherein the metal is aluminum or an aluminum alloy.

6. The method of claim 5, where the composition of matter is TG13-R.

7. The method of claim 5, where the composition of matter of TG14-R.

8. The method of claim 6, where R is methyl.

9. The method of claim 7, where R is methyl.

* * * * *